(12) United States Patent
Saravanamurugan et al.

(10) Patent No.: US 9,676,697 B2
(45) Date of Patent: Jun. 13, 2017

(54) CONVERSION OF CARBOHYDRATES TO LEVULINIC ACID ESTERS

(71) Applicant: DANMARKS TEKNISKE UNIVERSITET, Kgs. Lyngby (DK)

(72) Inventors: Shunmugavel Saravanamurugan, Kgs. Lyngby (DK); Anders Riisager, Taastrup (DK)

(73) Assignee: DANMARKS TEKNISKE UNIVERSITET, KGS. Lyngby (DK)

(*) Notice: Subject to any disclaimer, the term of this patent is extended or adjusted under 35 U.S.C. 154(b) by 0 days.

(21) Appl. No.: 15/051,288

(22) Filed: Feb. 23, 2016

(65) Prior Publication Data

US 2016/0168070 A1 Jun. 16, 2016

Related U.S. Application Data

(63) Continuation of application No. 14/418,798, filed as application No. PCT/EP2013/066281 on Aug. 2, 2013, now Pat. No. 9,290,429.

(30) Foreign Application Priority Data

Aug. 2, 2012 (EP) ..................... 12179076

(51) Int. Cl.
  *C07C 51/09* (2006.01)
  *C07C 67/00* (2006.01)
  *C12P 7/42* (2006.01)

(52) U.S. Cl.
  CPC .............. *C07C 67/00* (2013.01); *C07C 51/09* (2013.01); *C12P 7/42* (2013.01)

(58) Field of Classification Search
  None
  See application file for complete search history.

(56) References Cited

U.S. PATENT DOCUMENTS

| 4,236,021 A | 11/1980 | Hsu et al. |
| 2013/0324708 A1 | 12/2013 | de Sousa Dias et al. |
| 2015/0210622 A1 | 7/2015 | Saravanamurugan |

OTHER PUBLICATIONS

Saravanamurugan et al., Catalysis Communications 17 (2012) 71-75.*
Peng et al., Applied Energy 88 (2011) 4590-4596.*
Corma, A. et al., "Preparation of environmentally friendly alkylglucoside surfactants using zeolites as catalysts," Journal of Catalysis (1996) 161(2):713-719.
Peng, L. et al., "Conversion of carbohydrates biomass into levulinate esters using heterogeneous catalysts," Applied Energy, Elsevier Science Publishers (2011) 88(12):4590-4596.

(Continued)

*Primary Examiner* — Karl J Puttlitz
(74) *Attorney, Agent, or Firm* — Michael Best & Friedrich LLP

(57) ABSTRACT

The present invention relates to the field of converting carbohydrates into levulinic acid, a platform chemical for many chemical end products. More specifically the invention relates to a method for converting carbohydrates such as mono-, di- or polysaccharides, obtained from for example biomass production into a suitable levulinic acid ester in the presence of a zeolite or zeotype catalyst and a suitable alcohol, and the ester may be further converted into levulinic acid if desired.

21 Claims, 3 Drawing Sheets

(56) References Cited

OTHER PUBLICATIONS

Saravanamurugan, S. et al., "Solid acid catalysed formation of ethyl levulinate and ethyl glucopyranoside from mono- and disaccharides," and Supplemental Information, Catalysis Communications, Elsevier Science (2011) 17:71-75.
International Search Report for Application No. PCT/EP2013/066281 dated Sep. 13, 2013 (4 pages).
International Preliminary Report on Patentability for Application No. PCT/EP2013/066281 dated Oct. 15, 2014 (15 pages).
Holm et al., "Conversion of Sugars to Lactic Acid Derivatives Using Heterogeneous Zeotype Catalysts," Science (2010), 328(5978), 602-60.
Dewent citation for WO 2012091570, Derwent Accession No. 2012-H6441 Oi, Copyright ©2015 Thomson Reuters.
United States Patent Office Notice of Allowance for U.S. Appl. No. 14/418,798 dated Nov. 9, 2015 (7 pages).
United States Patent Office Action for U.S. Appl. No. 14/418,798 dated May 14, 2015 (10 pages).

\* cited by examiner

CONVERSION OF CARBOHYDRATES TO LEVULINIC ACID ESTERS

CROSS-REFERENCE TO RELATED APPLICATION(S)

This is a continuation of U.S. patent application Ser. No. 14/418,798, filed on Jan. 30, 2015, which is a U.S. national stage entry of International Patent Application No. PCT/EP2013/066281, filed on Aug. 2, 2013, which claims priority to European Patent Application No. 12179076.0, filed on Aug. 2, 2012, the entire contents of all of which are fully incorporated herein by reference.

FIELD OF THE INVENTION

The present invention relates to the field of converting carbohydrates into levulinic acid, a platform chemical for many chemical end products. More specifically the invention relates to a method for converting carbohydrates such as mono-, di- and polysaccharides, obtained from for example biomass production into a suitable levulinic acid ester in the presence of a suitable solid acid catalyst and a suitable solvent, and the ester may be further converted into levulinic acid if desired.

BACKGROUND OF THE INVENTION

Today most organic chemicals are being produced by catalytic transformations of fossil resources such as oil, coal and natural gas. Within a few decades, the availability of these fossil resources is projected to decrease thus making it imperative to use alternative carbonaceous resources as feedstock. Carbohydrates are abundant and inexpensive carbonaceous resources available in nature. Since carbohydrates constitute a renewable and carbon neutral resource, it has become increasingly important to find feasible ways to convert them into useful chemicals such as 5-hydroxymethylfurfural (HMF), lactic acid, levulinic acid, and the like.

Levulinic acid has in particular been recognized as an important bio-derived platform chemical that may provide a source to produce chemicals and fuels (U.S. Pat. No. 5,859, 263). Levulinic acid is also useful as a solvent, food flavoring agent, plasticizer, resin intermediate and building block for, e.g. tetrahydrofuran and succinic acid (C. K. Shu, B. M. Lawrence, *J. Agric. Food Chem.* 1995, 43, 782-784).

To produce levulinic acid, carbohydrates are traditionally being treated with aqueous mineral acid ($H_2SO_4$ and HCl) at atmospheric pressure at 100° C. (V. Sunjik, J. Horvat, B. Klaic, *Kem. Ind.* 1984, 33, 599-606). This method usually yields about 40% of levulinic acid. The yield of levulinic acid may further be improved to 60-70% by continuous flow conditions at higher temperatures and pressures using $H_2SO_4$ as catalyst (WO 89/10362 and WO 96/40609). S. Saravanamurugan, O. N. Van Buu, A. Riisager, *ChemSusChem* 2011, 4, 723-726, disclose conversion of mono- an disaccharides to ethyl levulinate with sulfonic acid-functionalized ionic liquids. However, a major drawback in these processes is tedious work-up during the separation stages. S. Saravanamurugan, A. Riisager, *Catal. Commun.* 2012, 17, 71-75 also disclose conversion of fructose to ethyl levulinate with sulfonic acid-functionalized SBA-15 catalysts.

Acidic ion-exchange resins have also previously been used as catalysts for the transformation of sucrose to levulinic acid (R. A. Schraufnagel, H. F. Rase, *Ind. Eng. Prod. Res. Dev.* 1975, 14, 40-44). Major disadvantages for these systems are moderate yields of levulinic acid of about 25% and maximum operation temperature around 150° C. due to thermal instability of the resin catalyst.

K. Lourvanij, G. L. Rorrer, *J. Chem. Technol. Biotechnol.* 1997, 69, 35-44 found Y-type zeolites to give moderate yields of levulinic acid (and minor amounts of HMF) when investigated as catalysts for the dehydration of fructose at temperatures between 110 and 160° C. In contrast K. Lourvanij, G. L. Rorrer, *Appl. Catal. A* 1994, 109, 147-165, found that a Fe-pillared montmorillonite catalyst was very active and able to convert glucose quantitatively, though with low selectivity of 20% to levulinic acid. Instead a much higher amount of formic acid as well as a significant amount of coke was observed in this study.

Zeolites are tridimensional crystalline aluminosilicates with the following formula in the as-synthesized form: $xM_{2/n}O.xAl_2O_3.ySiO_2.WH_2O$ where M is a cation which can belong to the group IA or IIA or can be an organic cation, while n is the cation valence, and W represents water contained in the zeolite voids. Crystalline structures of the zeolite type but containing tetrahedrally coordinated Si, Al, P, as well as transition metals and many group elements with the valence ranging from I to V such as, B, Ga, Fe, Cr, Ti, V, Mn, Co, Zn, Cu, etc., have been synthesized with the generic name of zeotypes, including $AlPO_4$, SAPO, MeAPO, and MeAPSO type molecular sieves.

The main characteristic of the zeolites and zeotypes is that the tetrahedral primary building blocks are linked through oxygen producing a three-dimensional network containing channels and cavities of molecular dimensions.

Considering the channel size they are conventionally defined as ultralarge (>12-membered rings) with a free diameter above 8 Å, large (12-membered rings) with a free diameter of 6-8 Å, medium (10-membered rings) with a free diameter of 4.5-6 Å, or small (8-membered rings) with a diameter of 3-4.5 Å, pore materials depending on the smallest number of O, Al and Si atoms that limits the pore aperture of their largest channel. Examples of zeolites and zeotypes with different pore size are given in Table 1. The system of channels of these molecular sieves produces solids with very high surface area and pore volume, which are capable of adsorbing great amounts of substrate/reactants. This fact combined with the possibility to generate active sites inside of the channels and cavities of zeolites and zeotypes produces a very unique type of catalyst, which by itself can be considered as a catalytic microreactor.

In a catalytic reaction the reactant follows a sequence of events before it becomes a desorbed product. In the case of a zeolite, the sequence is diffusion of reactant through the zeolite micropores to reach an active site, adsorption of reactant on the active site, chemical reaction to give the adsorbed product, desorption of the product, and, finally, diffusion of the product through the zeolite channels. In the case of carbohydrate reactions on zeolites and zeotypes, where the size of a molecule closely matches the pore size, it is reasonable to think that the first step in the catalytic process, i.e. the diffusion of the reactant, can play an important role in the overall rate of the reaction observed. The configurationally diffusion is strongly dependent on the site and nature of the reactant, intermediates, product, the type of catalyst, and temperature.

TABLE 1

Zeolites and Zeotypes and Their Ring Size for the
Major Channel (taken from Chemical Reviews, 1995, 95, 559-614)

| Catalyst type | Framework struct.type (IUPAC CODE) | type species | ring members |
|---|---|---|---|
| ultralarge pore | CLO | cloverite | 20 |
| | | JDF-20 | 20 |
| | UFI | VPI-5, MCM-9, AlPO$_4$-54 | 18 |
| | AET | AlPO$_4$-8, MCM-37 | 14 |
| large pore | FAU, EMZ | cubic and hexagonal faujasite, SAPO-37 | 12 |
| | BEA | beta | 12 |
| | MOR | mordenite | 12 |
| | OFF | offretite | 12 |
| | MAZ | mazzite, omega, ZSM-4 | 12 |
| | LTL | Linde Tpe L | 12 |
| | MTW | ZSM-12, MCM-22 SSZ-26, SSZ-23 | 12 |
| | AFI | AlPO$_4$-5, SAPO$_4$-5 | 12 |
| | ATO | AlPO$_4$-31, SAPO-31 | 12 |
| | AFR | SAPO-40 | 12 |
| | AFS | MAPSO-46 | 12 |
| | AFY | COAPO-50 | 12 |
| | ATS | MAPO-36 | 12 |
| medium pore | MFI | ZSM-5, silicate | 10 |
| | MEL | ZSM-11 | 10 |
| | FER | Ferrierite | 10 |
| | | ZSM-48 | 10 |
| | MTT | ZSM-23 | 10 |
| | TON | ZSM-222, theta I | 10 |
| | HEU | clinoptilolite | 10 |
| | AEL | AlPO$_4$, SAPO-11 | 10 |
| | AFO | AlPO$_4$-41 | 10 |
| small pore | LTA | A | 8 |
| | ERI | erionite, AlPO$_4$-17 | 8 |
| | CHA | chabazite | 8 |
| | KFI | ZK-5 | 8 |
| | RHO | RhO, BeAsPO-RHO | 8 |
| | AEI | AlPO$_4$ | 8 |
| | AFT | AlPO$_4$-52 | 8 |
| | ANA | AlPO$_4$-24 | 8 |
| | APC | AlPO$_4$-C, AlPO$_4$-H3, MCM-1 | 8 |
| | APD | AlPO$_4$-D | 8 |
| | ATT | AlPO$_4$-33, AlPO$_4$-12-TAMU | 8 |
| | ATV | AlPO$_4$-25 | 8 |
| | AWW | AlPO$_4$-22 | 8 |
| | | AlPO$_4$-12 | 8 |
| | | AlPO$_4$-14 | 8 |
| | | AlPO$_4$-14A | 8 |
| | | AlPO$_4$-15 | 8 |
| | | AlPO$_4$-21 | 8 |
| | ATN | MAPO-39 | 8 |
| | CHA | SAPO-34, COAPO-44, COAPO-47, ZYT-6 | 8 |
| | GIS | MAPSO-43 | |
| | LTA | SAPO-42 | |

The flexibility in changing the adsorption characteristics of zeolites will allow discrimination between competing reactants, intermediates and products by modifying their relative adsorption interaction. Indeed, in the case of zeolites there are structures with low framework Si/Al ratios, and therefore with a large number of compensating cations which will produce very high electrostatic fields and field gradients in the channels and cavities. On the other hand, samples can be synthesized with high framework Si/Al ratios in which mainly dispersion forces are present, while very little or no influence from electrostatic fields and polarization forces will exist. In other words one could prepare zeolites with a very strong hydrophilic character which would preferentially sorb polar molecules or, on the opposite, with strong hydrophobic properties. In this way, one can change not only the total sorption capacity but also the relative adsorption, within the pores of the zeolite, of molecules with different polarity. This can be achieved by changing the framework Si/Al ratio by either synthesis or post synthesis treatments.

W. E. Farneth, R. J. Gorte have in Chem. Rev., 1995, 95, 615-635, discussed methods of characterizing the acidity of zeolites. The effect of both Brønsted and Lewis sites in a solid acid catalyst, such as zeolites, play an important role, but they are difficult to separate. The Brønsted effect relates to sites with a tendency to give up a proton, while the Lewis effect relates to sites with an electron-accepting property. However, zeolites are not molecules with a single type of acidic proton delivering and/or electron accepting feature, but rather collections of proton donor and/or electron accepting sites within a continuous framework. There may be a range of proton/electron affinities for a given zeolite. Different zeolites show very different specific rates of reactions, for example highly known in the field of hydrogen cracking. For low-silica faujasites, like HY, the catalytic activity increases as Al is removed from the lattice. In high-silica (Si/Al>10) materials like HZSM-5 and faujasites, however, catalytic activities increase linearly with Al-content for a number of reactions, particular in cracking.

S. Saravanamurugan, A. Riisager, in *Catal. Commun.* 2012, 17, 71-75 have shown that sulfonic acid functionalized SBA-15 is efficient and sulfonated zirconium less efficient in a catalyzed formation of ethyl levulinate from biomass-derived fructose and glucose. The non-functionalized zeolites ZSM-5, Y, beta and mordenite resulted in very little or no formation of ethyl levulinate. The experiments were performed in an ace pressure tube without pressurizing the reaction mixture contrary to the present method (Table 10). Compared to the zeolites of which some are available in nature in their pristine forms, the sulfonic acid functionalized materials are unnatural materials which are cumbersome to prepare and prone to loss of sulfonic acid functionality upon thermal treatment and recycling.

SUMMARY OF THE INVENTION

To circumvent the drawback of thermal instability of certain solid catalysts, tedious separation steps when applying liquid catalysts, prevention of build-up of coke in the catalyst, use of functionalized catalysts and to improve the yield of levulinate of biomass-derived carbohydrates, the present invention has explored the use of commercially available solid acid catalysts, such as zeolites and zeotypes, for the conversion of glucose and its naturally occurring biological isomers and polymer precursors, which may be obtained for example from pre-treated biomasses, into a levulinic acid ester, which again can be converted into levulinic acid if desired.

In accordance with the aim of the invention, the present invention relates to a method of converting a carbohydrate, for example a mono-, di- or polysaccharide into a levulinic acid ester, wherein the saccharide or a mixture of saccharides is heated in the presence of a suitable zeolite or zeotype catalyst and a suitable solvent.

In a first aspect of the invention, the saccharides to be converted in accordance with the present invention are mono-, di- and polysaccharides or a combination thereof, preferably derived from a biomass production. In particular C6-sugars (hexoses) and di- and polysaccharides including such C6-sugars (hexoses) may be converted by the present method. More particular, glucose, fructose and mannose, even more particular glucose and mannose and most particular glucose are/is the preferred monosaccharide(s) for use as a reactant (substrate) in the method according to the present invention. However C5-sugars (pentoses) may also be converted according to the present invention. Pentoses may be xylose, which is a building block in hemicellulose, ribose, arabinose, xylulose and ribulose. Important disaccharides are in particular sucrose, maltose (hydrolysis product of the polysaccharide starch) and cellobiose (hydrolysis product of the polysaccharide cellulose). Other disaccharides are lactose, lactulose and trehalose. As important polysaccharides may be mentioned inulin, cellulose and starch, in particular inulin, a poly-fructose polymer, which may be found for example in many plant roots, may be converted directly by the present method.

In a second aspect of the invention, the solid acid catalysts suitable for conversion of saccharides derivable from biomass are selected from the group of zeolite or zeotype catalysts comprising large pores (12 membered rings catalysts) with a pore size diameter between 6 and 8 Å. Suitable zeolites can be selected from Table 1. Illustrative for the present invention, faujasites (HY) and BEA (Hbeta) zeolites have shown the advantage of using zeolite or zeotype catalysts with pores between 6 and 8 Å.

In addition to pore size, the solid catalysts for use in the present method must also comprise an effective number of acid sites. The acid sites are divided into two different types of sites, a medium site (type 1) and a strong site (type 2). In one embodiment of the present invention, the ratio between type 1 and type 2 is below 1:1.3. More preferred, the ration is below 1:1.1, and even more preferred, the ration is between 1:0.3 and 1:1.1. The total amount of acid sites is above 150 µmol/g, more particular above 200, and even more particular over 250 µmol/g, measured by the TPD-$NH_3$ method. An optimum number for the total amount of acid sites seems to be around 800 µmol/g, however numbers of acid sites above 500, or above 700 may also result in sufficiently good results to be selected, especially if other properties of the catalyst in connection with the chosen saccharide and/or solvent are beneficial. Above 800 µmol/g the efficiency of the catalyst seems to drop slowly. It has turned out, that of the tested (and illustratively selected) catalysts, in particular the solid catalysts HY 2.6, HY 6, HY 30, Hbeta 12.5 and Hbeta 19 are efficient, and more particular, the solid catalysts HY 6 and Hbeta 19 have resulted in excellent yields in converting the chosen saccharides, such as glucose into levulinic acid esters. The numbers refer to the Si/Al ratios.

In a third aspect of the present invention, the conversion of saccharides over a suitable zeolite or zeotype catalyst is performed in the presence of a suitable alcohol. Many different alcohols may be used, and may be selected in order to obtain a particular ester of levulinic acid, and/or for solubility and/or purification purposes. However, the efficiency seems to decrease with increasing number of carbon atoms in the alcohol, which may be due to changed polarity and/or bulkiness. Thus, C1-C4 alcohols are particular useful, C1-C3 alcohols even more useful and methanol and ethanol are the most efficient solvents. Accordingly, ethyl levulinate (ELevu) and methyl levulinate (MLevu) are the preferred levulinic acid esters produced according to the present method.

Conversion of saccharides in the presence zeolite or zeotype catalysts and a suitable alcohol requires a certain elevated temperature in the reaction vessel (reactor). A suitable temperature is above 100° C.; preferably at or above 120° C., more preferably at or above 140° C.; and most preferable at or above 160° C. for the conversion of most mono- and disaccharides. For polysaccharides a temperature at or above 180° C., preferably at or above 200° C. appears to be needed.

Further, the conversion process needs to run in the reactor for a time sufficient to obtain a desired conversion rate or yield. A reaction time may be 1 hour, but should preferably be at least 3 hours, for example at least 20 hours or even more.

The levulinic acid ester produced according to the present invention may be converted into levulinic acid by hydrolysis in a treatment with a base, acid or enzyme.

DRAWINGS

DETAILED DISCLOSURE OF THE INVENTION

Figure 1:
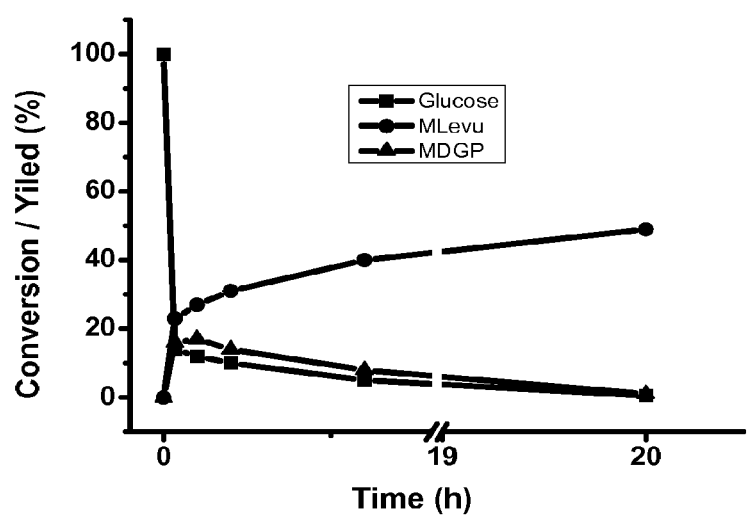
FIG. 1 shows a time-course study on the conversion of glucose to methyl levulinate (each set of data's are from individual experiment).

The present invention concerns a method for converting a saccharide, such as a mono-, di- or polysaccharide or any combination thereof into a levulinic acid ester (alkyl levulinate).

The present method comprises the steps of providing a saccharide or combination of saccharides in a suitable reactor together with a suitable solvent and a suitable solid acid catalyst selected from zeolites and zeotypes, and heating said saccharide(s) in the presence of the catalyst and the solvent.

The reactor is preferably a pressure batch reactor wherein the reaction mixture is pressurized during the conversion in order to maintain the solvent below the boiling point at the applied temperature.

Boiling Point of Alcohols at Different Pressure with Argon

| Pressure (bar) | Methanol bp (° C.) | Ethanol bp (° C.) |
| --- | --- | --- |
| 1 | 64.7 | 78.37 |
| 2 | 83 | 98 |
| 4 | 103 | 120 |
| 10 | 133 | 153 |
| 20 | 160 | 182 |

Selecting solid acid catalysts suitable for converting saccharides into levulinic acid ester is based on many properties of the catalyst in addition to properties of the selected solvent and the saccharide selected for conversion. Other factors to consider are reaction conditions such as heat, reaction time and reaction vessel. In the examples of the present invention, the reaction mixture in the pressure batch reactor is pressurized to 20 bar with argon. Other pressures may be applied in accordance with the selected temperature.

DEFINITIONS

A carbohydrate is an organic compound that consists only of carbon, hydrogen, and oxygen, usually with a hydrogen: oxygen atom ratio of 2:1 and the empirical formula $C_m(H_2O)_n$. The term is most common in biochemistry, where it is a synonym of saccharide. The carbohydrates (saccharides) are divided into four chemical groupings: monosaccharides, disaccharides, oligosaccharides, and polysaccharides. In general, the monosaccharides and disaccharides, which are smaller (lower molecular weight) carbohydrates, are commonly referred to as sugars. The terms carbohydrate, saccharide and sugar may be used interchangeably throughout the text.

Monosaccharides are the simplest carbohydrates in that they cannot be hydrolyzed to smaller carbohydrates. They are aldehydes (aldoses) or ketones (ketoses) with two or more hydroxyl groups. The general chemical formula of an unmodified monosaccharide is $(C.H_2O)n$, literally a "carbon hydrate". Monosaccharides with five carbon atoms (C5) are called pentoses and with six carbon atoms (C6) are hexoses. For example, glucose is an aldohexose (a six-carbon aldehyde), ribose is an aldopentose (a five-carbon aldehyde), and fructose is a ketohexose (a six-carbon ketone).

Two joined monosaccharides are called a disaccharide and these are the simplest polysaccharides. Examples include sucrose and lactose. They are composed of two monosaccharide units bound together by a covalent bond known as a glycosidic linkage formed via a dehydration reaction, resulting in the loss of a hydrogen atom from one monosaccharide and a hydroxyl group from the other. The formula of unmodified disaccharides is $C_{12}H_{22}O_{11}$. There are numerous kinds of disaccharides. In the present invention, the most important are: sucrose (glucose linked to fructose via a $\alpha(1\rightarrow2)\beta$ bond), maltose (two glucose units linked via a $\alpha(1\rightarrow1)\alpha$ bond, a hydrolysis product of the polysaccharide starch) and cellobiose (two glucose units linked via a $\beta(1\rightarrow4)$ bond, a hydrolysis product of the polysaccharide cellulose).

An oligosaccharide is a saccharide polymer (a polysaccharide) containing a small number (typically 2 to 10) of component monosaccharides. In the present invention oligosaccharides are considered a polysaccharide.

Polysaccharides are composed of long chains of monosaccharide units bound together by glycosidic bonds. Polysaccharides contain more than two monosaccharide units. They range in structure from linear to highly branched. Polysaccharides are often quite heterogeneous, containing slight modifications of the repeating unit. Depending on the structure, these macromolecules can have distinct properties from their monosaccharide building blocks.

Catalyst

As discussed above, many properties of a catalyst define the functionality of the catalyst. In the present invention, focus has been put on two important measurable properties when selecting catalysts for use in the present method. The first property is the pore size. By testing different catalysts, it has become clear, that a large pore size is needed in order to allow access of the substrate and solvent through the channels into the interior part of the catalyst and to allow the resulting levulinate to leave the catalyst after conversion. The second important property is the acidity of the catalyst. Many other properties are however involved in a successful conversion, such as adsorption properties of the pores and cavities inside the catalyst and polarity of the substrate. As also discussed above and in the background literature, it is not possible to predict optimal selection of catalysts or catalyst properties for conversion of carbohydrates. The skilled person would need to try out many different catalysts in the hope of finding suitable solid catalyst(s). Only if suggestions have been made in the art, such as predefined properties of useful catalysts in relation to certain substrates, the skilled person may select catalysts with expected properties suitable for his need. The present invention addresses a way of pre-selecting catalysts with the right properties such as pore size and acidity, measurable features that define useful catalysts for the conversion of mono-, di- or polysaccharides to levulinic acid ester.

The group of materials with a molecule sieves structure possessing catalytic properties useful in the method according to the present invention is the so-called zeolites. In 2011, over 40 naturally occurring zeolite frameworks were known. In addition over 180 synthetic zeolites and zeotypes with different pore sizes and structures have been produced over the time. According to the present invention, only zeolites and zeotypes with large pores (by definition between 6 and 8 Å) are efficient for use in the present method of converting carbohydrates (saccharides) into levulinic acid esters. This means that in practice, the pore size diameter should be above 6 Å. Table 1 summarizes a number of zeolite and zeotype catalysts.

Two commercially available zeolite catalysts with large pores, H-Y (a fajusite (FAU) catalyst) and H-beta (a BEA catalyst) were selected to illustrate the present invention as shown below. This is by no means to be seen as a limitation to these two types of catalysts. Many other zeolite and zeotype catalysts with large pores (see Table 1) may be used as catalyst in method of the present invention.

Fajusite

Fajusite (FAU) zeolites are divided into two types X and Y. Y zeolites can be dehydrated and dealuminated to produce ultra-stable Y (USY) zeolites which are commercially available. Zeolite Y is classified under large pore zeolites since it has pore diameter of 7.4 Å. Zeolite Y has a 3-dimensional pore structure with pores running perpendicular to each other in the x, y, and z planes, and is made of secondary building units 4, 6, and 6-6. The pore diameter is as large as 7.4 Å since the aperture is defined by a 12 member oxygen ring, and leads into larger cavities of a diameter of 12 Å. The cavity is surrounded by ten sodalite cages (truncated octahedra) connected on their hexagonal faces. Commercially available Y (H-Y or HY) catalysts are often named H-VUSY (e.g. H-VUSY-6), H-SDUSY (e.g. H-SDUSY-30) or H-USY, indicating specific preparation before use, for example, steam treatment.

Beta Zeolite

Zeolite Beta (BEA; H-beta) is three-dimensional large-pore zeolites with a 12-membered ring system. Zeolite BEA is the only large-pore zeolite having chiral pore intersections. The pore structure of BEA consists of 12-membered rings interconnected by cages formed by the intersections of the channels. The channel system of zeolite Beta has pore diameters of about 7 Å, which are similar to other large-pore molecular catalysts such as FAU.

Si/Al Ratio

The adsorption characteristics of zeolites will allow discrimination between competing reactants and products by modifying their relative adsorption interaction, which can be done for example by changing the Si/Al ratios in the catalytic structures. This can be achieved by changing the framework Si/Al ratio by either synthesis or post synthesis treatments. For example, alkaline treatment of zeolites may lead to extensive silicon extraction at mild treatment conditions. This leads to a lower Si/Al ratio, but also impacts on the microporous and acidic properties of the resulting catalyst. As will become clear from the present invention, optimization of the Si/Al ratio is of very high importance for successful conversion of saccharides to levulinic acid ester. It will also become clear, that an optimal window of Si/Al ratios identified for one zeolite family does not necessary apply to other zeolite families. The optimal Si/Al window needs to be established for each zeolite family individually. Extraction of silicon may lead to substantial mesoporosity of the treated catalyst and presumably an improved transport of the reactants.

Acidity

In addition to pore size, the catalysts for use in the present method should have the right acidic properties. One way of securing, controlling and/or changing acidic properties is by selecting a catalyst with the right Si/Al ratio, i.e. Si/Al ratio window, or changing the ratio of other catalysts with less efficient structures. The complexity of the catalyst structures also lead to different acids sites with different strengths in a particular zeolite framework. It has turned out, that the two illustrative zeolites possess "medium" (type 1) and a "strong" (type 2) acid sites as measured by the $NH_3$-TPD method. A measure of the acidic properties of a certain catalyst for use in the present invention is thus the number of acidic sites and the ratio between type 1 and type 2 acid sites.

Adsorption of volatile amines such as $NH_3$ can be used to determine the number of acidic sites on a solid catalyst. $NH_3$ is adsorbed on both Brønsted and Lewis sites if both types of acid sites are catalytically active. $NH_3$ chemically adsorbed on the catalyst is evacuated by thermal desorption (TPD) and the acid strength calculated according to the proportion evacuated at various temperatures. The two acid sited provide for a strong acid site (type 2) and a medium acid site (type 1), the adsorption being stronger at the strongest acid site, thus calling for a higher temperature for desorption. The $NH_3$-TPD method is a conventional method that is extensively used to measure the acidity of solid catalysts (Chem. Rev., 1995, 95, 559-614).

The number of acidic sites in some of the catalysts tested in a method according to the present invention has been measured according to the $NH_3$-TPD method (example 11) and the results are shown in Table 2.

TABLE 2

Influence of number of acid sites and pore type of the zeolites on the yield of methyl levulinate.

| Catalyst | Pore type | Si/Al ratio | Acid sites type 1 (100-270° C.) (µmol/g) | Acid sites type 2 (270-500° C.) (µmol/g) | Total acid sites (µmol/g) | Acid sites type 1: type 2 ratio | Methyl levulinate (%) |
|---|---|---|---|---|---|---|---|
| H-Y | Large pores | 2.6 | 699 | 252 | 951 | 1:0.36 | 32 |
| | | 6 | 461 | 374 | 835 | 1:0.81 | 49 |
| | | 30 | 182 | 165 | 347 | 1:0.91 | 37 |
| H-Beta | | 12.5 | 563 | 292 | 855 | 1:0.52 | 44 |
| | | 19 | 440 | 366 | 806 | 1:0.83 | 47 |
| | | 150 | 71 | 76 | 147 | 1:1.07 | 10 |
| H-ZSM-5 | Medium pores | 40 | 211 | 240 | 451 | 1:1.14 | 6 |

In accordance with the results obtained by the $NH_3$-TPD method, the effective number of acid sites needs to be above 150 µmol/g, more particular or above 200 µmol/g and even more particular above 300 µmol/g. It can also be seen that there appears to be an optimum for the amounts of acid sites around 800 µmol/g, above which the efficiency of the catalyst seems to decrease. An amount of 500 or 700 µmol/g acid sites may be sufficient to obtain acceptable yields.

From table 2, it can be inferred that HY 6 and Hbeta 19 have almost the same ratio of acid sites type 1 and 2 (1:0.8), which catalysts gave the highest yields of methyl levulinate. For HY 30, the acid sites ratio (1:0.91) is higher than HY6 and Hbeta 12.5 giving lower yield of methyl levulinate (37%). Hbeta 12.5 with ratio of 1:0.52 gave slightly lower yield of methyl levulinate compared to HY6 and Hbeta 19. From these results, it can be understood that acid sites type ratio above 1:0.3, more particular between 1:0.3 and 1:1.2 and more particular between 1:0.3 and 1:1.1 or between 1:0.3 and 1:1 along with total acid sites above 200 could give significant yield of methyl levulinate. The optimum ratio window seems to be 1:0.5 to 1:0.9. Another interesting medium pore zeolite, HZSM-5(40) has been considered for comparison on the yield of methyl levulinate. Even though it has relatively large number of total acid sites and the acid sites ratio is within the range to have a good yield of methyl levulinate, it yielded only 6% of methyl levulinate because of bulky molecular transport limitations in the medium pore channels of ZSM-5.

In an initial experiment, the conversion of glucose to ethyl levulinate (ELevu) and methyl levulinate (MLevu) respectively over different zeolites was carried out in presence of the solvents ethanol or methanol. The results are presented in Table 3, and show that H-Y zeolite with a silicon to aluminum ratio of 2.6 yielded a relatively low amount of ELevu (15%), but interestingly yielded a high amount of MLevu (32%). H-Y zeolite with silicon to aluminum ratio of 6 gave 41% ELevu, and 49% MLevu respectively. H-Y zeolite with silicon to aluminum ratio of 30 gave 26% ELevu and 37% MLevu respectively.

TABLE 3

Catalytic conversion of glucose to
ethyl levulinate or methyl levulinate over zeolites
(see Examples 1 and 11 for experimental details; 160° C.; 20 hours)

| Catalyst[a] | Yield of ELevu (Conversion) (%) | Yield of MLevu (Conversion) (%) |
|---|---|---|
| HY (2.6) | 15 (>99) | 32 (>99) |
| HY (6) | 41 (>99) | 49 (>99) |
| HY (30) | 26 (>96) | 37 (93) |
| HBeta (12.5) | 27 (>99) | 44 (>99) |
| HBeta (19) | 28 (>99) | 47 (>99) |
| Hbeta (150) | 3 (74) | 10 (80) |
| HZSM-5 (40) | — | 6 (81) |
| No Catalyst | 0 (45) | <0.5 (77) |

[a]Numbers in the parenthesis are silicon to aluminum ratio

Two other zeolites, H-Beta, and HZSM-5, were also used for the conversion of glucose and the results are also shown in Table 3. The H-Beta zeolites with ratio of 12.5 and 19 gave 27 and 28% of ELevu and 44 and 47% of MLevu, respectively. Practically all glucose was converted. The H-Beta zeolite with ratio of 150 gave only 3% of ELevu and 10% MLevu, the conversion rate being 74-80% of the glucose after 20 hours at 160° C. The HZSM-5 zeolite with a Si/Al ratio of 40 gave only a yield of 8% of MLevu. HZSM-5 zeolite has a medium pore size (4.5-6 Å) which would appear to be the reason for the low yield.

The formation of ethyl levulinate can possibly be formed from glucose via three pathways as shown in scheme 1 (illustrated with ethanol as solvent): The first one, glucose can isomerize to fructose and subsequently reacted with ethanol to form ethyl-D-fructofuranoside (EDFF) (intermediate not confirmed yet) followed by dehydration to form HMF-ether and then rehydration to form ELevu. The second one, glucose can directly react with ethanol to form ethyl-D-glucopyranoside (EDGP) and then isomerise to EDFF and follows the same pathway as mentioned in the first one. Thirdly, after the isomerisation to fructose, it can directly dehydrate to form HMF, HMF-ether and then to ELevu. Methyl levulinate is most likely formed via the same pathways.

The importance of selecting the right catalyst (in combination with the right solvent) for a given carbohydrate substrate is illustrated by the conversion of glucose (Table 3) and fructose (Table 4) over different catalysts (and in the presence of different solvents). One of the reasons for a higher sensitivity in conversion of fructose compared to glucose seems to be that the predominant pathway for fructose to ELevu/MLevu is through the intermediates either HMF or EDFF (and not through EDGP/EDFF as for glucose, mannose and cellobiose), which could be responsible for more degradation or formation of more humins.

TABLE 4

Catalytic conversion of fructose
to methyl levulinate over different zeolites.

| Catalyst[a] | Conversion (%) | Yield of MLevu (%) |
|---|---|---|
| HY (2.6) | 99 | 32 |
| HY (6) | >99 | 51 |
| HBeta (12.5) | 99 | 44 |
| HBeta (19) | >99 | 48 |
| No Catalyst | 70 | 0.5 |

[a]Numbers in the parenthesis are silicon to aluminum ratio. (see example 2a-d and 11 for experimental details).

Durability of the Catalyst

Figure 2:
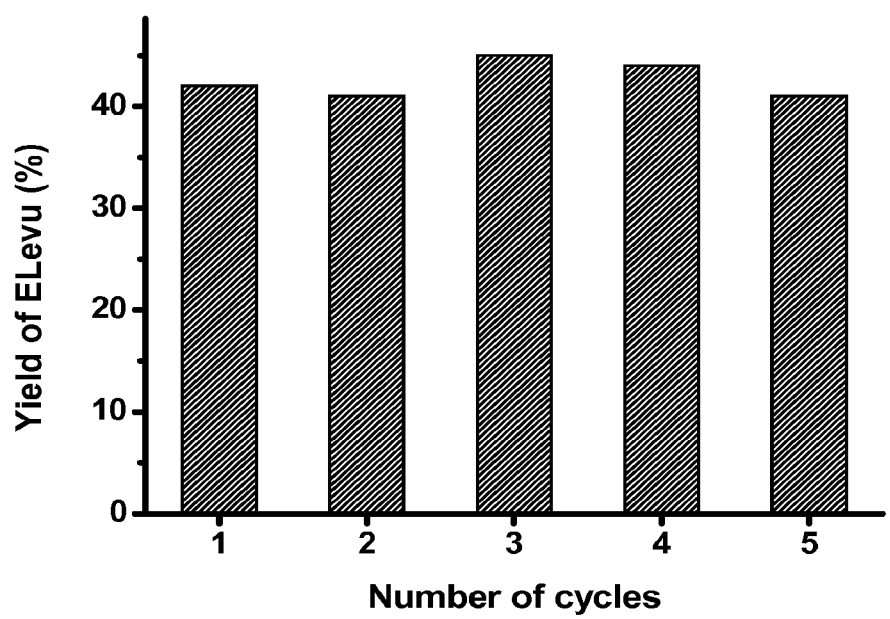
FIG. 2 shows recyclability of HY6 for glucose to ethyl levulinate.

It is industrially important to know the stability of a catalyst after repeated cycles. Based on this view point, HY6 was been tested for the conversion of glucose and sucrose to ELevu for five cycles (FIG. 2). After the first run, the yields of ethyl levulinate were 48 and 43% from glucose and sucrose, respectively. First run-through fifth, no significant changes in yields of ethyl levulinate from glucose and sucrose were observed. After the fifth use of HY6 catalyst, negligible changes in pore volumes and surface areas were observed. Likewise, a small decrease in surface area and a small increase in pore volume was observed after the fifth use of HY6 for sucrose, thus confirming the structural integrity of HY6 after five cycles.

Substrate

Carbohydrates such as mono-, di- and polysaccharides are abundant and inexpensive carbonaceous resources available in nature which, however, may be converted into useful chemicals, such as for example levulinic acid or esters thereof in order to be economically interesting. In the present invention conversion of simple sugars such as pentoses and hexoses, in particular glucose and its isomers to levulinate have been exploited. The product of the present method, levulinic acid ester or levulinate, may easily be converted into levulinic acid in a number of commonly and commercially attractive ways, including hydrolysis in the presence of a base, acid or suitable enzyme, e.g. a lipase, an esterase, etc. The substrate, e.g. glucose, fructose, sucrose, maltose, cellobiose, xylose, etc., may be provided after pretreatment of suitable biomass, such as straw, grass, wood, biowaste. Polysaccharides such as cellulose, hemicellulose, starch and inulin may be treated directly in the present method or after a pre-treatment to liberate mono and disaccharide (sugar) units. Such pretreatment is commonly known in the art.

Scheme 1. The plausible pathway for the formation ethyl levulinate from glucose.

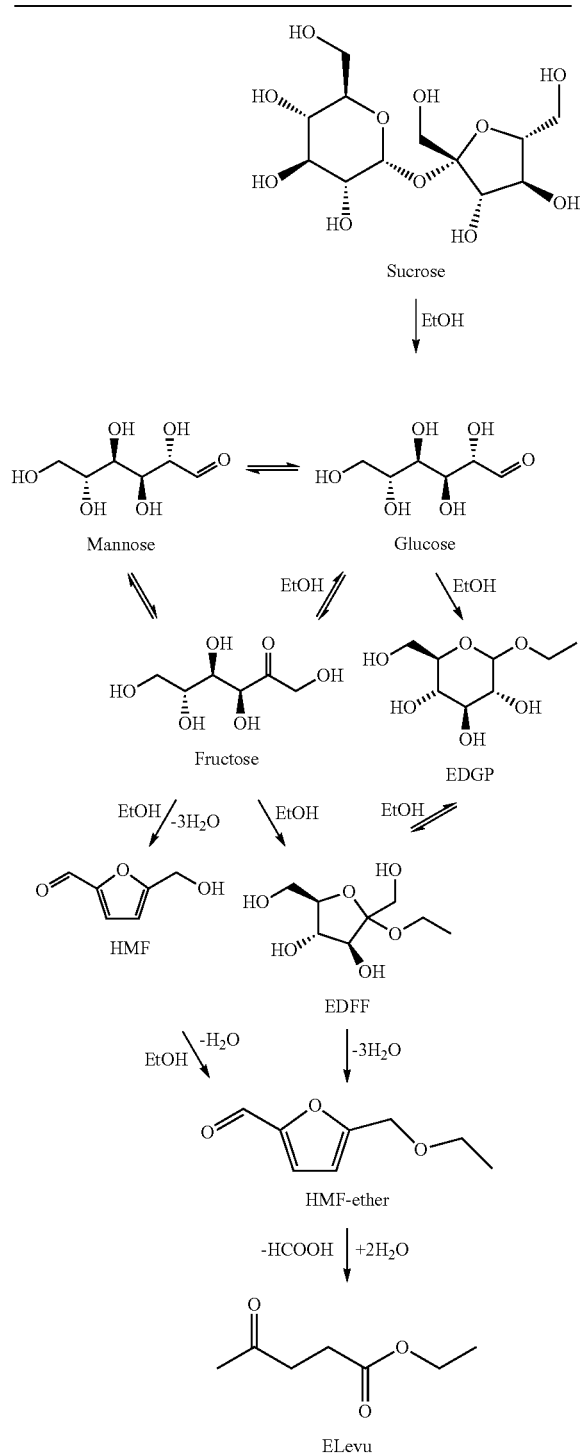

EDGP: ethyl-D-glucopyranoside.
EDFF: ethyl-D-fructofuranoside.
HMF: 5-hydroxymethyl furfural.

Under identical reaction conditions, other mono-, disaccharides related to glucose (Scheme 1) as well as some polysaccharides were also studied, and the yield of ELevu is shown in Tables 5 and 6.

TABLE 5

Catalytic conversion of mono-, di-, and polysaccharides to ethyl and methyl levulinate over H-Y6
(See Examples 1-8 for experimental details; 160° C.; 20 hours)

| Substrate | Yield of ELevu (Conversion) (%) | Yield of MLevu (Conversion) (%) |
| --- | --- | --- |
| Glucose | 41 (>99) | 49 (>99) |
| Fructose | 40 (>99) | 51 (>99) |
| Mannose | 44 (>99) | 53 (>99) |
| Sorbose | 47 (>99) | 51 (>99) |
| Sucrose | 35 (>99) | 49 (>99) |
| Cellobiose | 44 (>99) | 53 (>99) |
| Maltose | 33 (>99) | 41 (>99) |
| Xylose[b] | 11 (>99) | — |
| Inulin | 39 | 50 (>99) |
| Starch | 4 | 31 |
| Cellulose | 2 | 3 (NA) |

[b]A pentose (C5 sugar).

TABLE 6

Catalytic conversion of mono-, di-, and polysaccharides to ethyl and methyl levulinate over H-beta 19
(See Examples 1-6 for experimental details; 160° C.; 20 hours)

| Substrate | Yield of ELevu (Conversion) (%) | Yield of MLevu (Conversion) (%) |
| --- | --- | --- |
| Glucose | 28 (>99) | 47 (>99) |
| Fructose | 48 (>99) | 48 (>99) |
| Mannose | 25 (>99) | 35 (>99) |
| Sucrose | 34 (>99) | 44 (>99) |
| Cellobiose | 28 (>99) | 44 (>99) |
| Xylose[a] | 11 (>99) | — |
| Inulin | 34 | 47 (>99) |

[a]A pentose (C5 sugar).

As shown in scheme 1, the predominant pathway for fructose to ELevu is through the intermediates either HMF or EDFF which could be responsible for more degradation or formation of more humins. For glucose, mannose and cellobiose, the predominant pathway to form ELevu is through the formation of EDGP/EDFF. This is apparently supported by the time-course experiment that the formation of significant amount of EDGP from glucose after 10 minutes (FIG. 1).

The polysaccharide inulin, yielded more than 39% (H-Y) and 34% (H-beta) of ethyl levulinate and more than 50% (H-Y) and 47% (H-beta) of methyl levulinate thus implying that under this experimental conditions, inulin was able to dissolve and hydrolyze in ethanol and methanol and eventually, be converted into ethyl levulinate or methyl levulinate respectively. Low yields of ELevu were observed for starch and cellulose even at increased temperatures (Tables 5 and 8), however formation of 31% MLevu could be obtained for conversion of starch in the presence of methanol.

Solvent

Levulinic acid is an important source for producing useful chemicals and fuels. Levulinic acid may be produced as a bio-derived chemical by converting saccharides in the presence of water as previously described. However, as shown in the present application, under identical reaction conditions, the yield of levulinic acid is significantly reduced when water was used as solvent compared to use of an alcohol. The yield of levulinic acid was 11% along with 99% conversion of glucose (Table 7). A lot of other side products were also observed in HPLC including lactic acid, acetic acid and formic acid. Once these acids are formed, they may take part in the degradation of glucose and lead the reaction to form undesired products, thus decreasing the yield of levulinic acid.

The yield of levulinate ester increased substantially to 41% when ethanol was used as solvent and even to 49% when methanol was used as solvent. However, when propanol and butanol were used as solvent the yield of propyl and butyl levulinate was as low as 17 and 12% respectively, which could be due to predominant side reactions, changed polarity or bulkiness. It is therefore preferred to use methanol or ethanol as solvent in the method according to the present invention. A suitable pressure is applied to the reaction mixture in order to keep the boiling point below the applied temperature. An inert gas, such as argon may be used to pressurize the reaction chamber. A preferred pressure is about 20 bar, as shown in the examples.

TABLE 7

Catalytic conversion of glucose to levulinic acid and its esters over HY6 (See Example 1 for experimental details; 160° C.; 20 hours)

| Solvent | Conversion (%) | Yield of Levulinic acid ester (%) |
|---|---|---|
| Water | >99 | 11 |
| Methanol | >99 | 49 |
| Ethanol | >99 | 41 |
| Propanol | >99 | 17 |
| Butanol | >99 | 12 |

After conversion of glucose with the use of water as solvent, the HY6 catalyst was subjected to $N_2$ sorption analysis. It revealed that the surface area was decreased from 657 to 595 $m^2/g$ and pore volume decreased from 0.2295 to 0.2164 $cm^3/g$, thus implying that a relatively significant loss of structural integrity in the zeolite lattice occurred during the process. These results show the importance of using alcohol, preferably methanol or ethanol, as solvent to obtain levulinic acid esters rather than to produce levulinic acid in water.

Method Conditions

The method in the present invention can be run in any kind of pressure batch reactor that can withstand high pressure that may develop during heating of reactants, including the selected alcohol. A pressure of 20 bar is applied in the examples. A thermocouple and stirrer should be connected in the reactor to monitor reaction temperature and rotation per minute (rpm).

The catalytic experiments could possibly also be performed in suitable fixed bed reactors, loop reactors or in pressure and temperature controlled microwave reactors to decrease the reaction time.

For production of levulinic acid esters in commercial scale, large reaction vessels suited for the disclosed method can be applied by the skilled person. The up-scaling and optimization of the process is very important and may include adjustment of many process parameters known by a process engineer.

Process Temperature

A very important aspect of the present invention is the choice of the optimum temperature suited for the chosen catalyst, and reactants, i.e. saccharide(s) and solvent. In an experiment (Example 9), the conversion of the monosaccharide glucose, was tested in the presence of H-Y 6 and methanol at different temperatures, in order to optimize the process conditions. The results are shown in Table 8. The optimum temperature for the tested combination would appear to be above 120° C., with good result at 120° C., an even better result at 140° C. At 160° C. the best results are seen with the tested catalyst, monosaccharide and solvent. Raising the temperature to 180° C. seems to decrease the output of MLevu, thus indicating an optimum temperature around 160° C. The conversion was run for 20 hours and the pressure being 20 bar (290 psi). Dependent on the complexity of the saccharide (di- and polysaccharides), it may be beneficial to the conversion rate and yield to increase the temperature to above 160° C., for example to 180° C. or 200° C. Alternatively, di- and polysaccharides may be hydrolyzed to obtain suitable mono- and/or disaccharides for use in the present invention.

TABLE 8

Catalytic conversion of substrates to methyl levulinate over HY6 (see Example 10 for experimental details; 20 hours, 20 bar)

| Temperature (° C.) | Substrate | Conversion (%) | Yield of MLevu (%) |
|---|---|---|---|
| 100 | Glucose | 66 | 13 |
| 120 | Glucose | 90 | 33 |
| 140 | Glucose | 98 | 47 |
| 160 | Glucose | >99 | 49 |
| 180 | Glucose | >99 | 39 |
| 160 | Cellulose | — | 3 |
| 180 | Cellulose | — | 9 |
| 200 | Cellulose | — | 13 |

TABLE 10

Results from pressure batch reactor (autoclave) experiments at different pressure of argon.

| Pressure (bar) | Conversion of Fructose (%) | Yield of Elevulinate (%) |
|---|---|---|
| 20 | 99 | 15 |
| No pressure* | >99 | 7 |

Comparison with S. Saravanamurugan, A. Riisager, in Catal. Commun. 2012, 17, 71-75.
Experimental conditions:
Fructose = 0.5400 g;
Catalyst weight = 0.160 g (H-beta 12.5);
Ethanol: 8.0 g;
Temperature = 140° C.;
Time = 20 h;
Pressurized with Ar;
*not pressurized with Ar Process Time In an experiment (Example 8), the conversion of the monosaccharide glucose, was tested in the presence of HY-6 and methanol at different process times, in order to further optimize the process conditions. The results are shown in Table 9. The optimum process time for the tested combination would appear to be above 10 minutes, with good results after 10 minutes, even better results after 30 minutes, 1 hour, 3 hours and the best result after 20 hours. The results also show that for the tested combination, in order to have a full conversion of the glucose, a process time of above 3 hours is needed. Only the results obtained after 20 hours show more than 99% conversion. Process time should be selected in combination with the chosen process temperature in order to optimize the process.

TABLE 9

Catalytic conversion of
glucose to methyl levulinate over HY-6
(see Example 9 for experimental details; 160° C.)

| Time | Conversion (%) | Yield of MLevu (%) |
|---|---|---|
| 10 min | 86 | 23 |
| 30 min | 88 | 27 |
| 1 hour | 90 | 31 |
| 3 hours | 95 | 40 |
| 20 hours | >99 | 49 |

Levulinic acid esters may be converted into levulinic acid by any known way of hydrolyzing a ester, including the use of a base, an acid or any suitable enzyme, such as an esterase a lipase, etc.

EXAMPLES

Example 1a-l

A 50 ml autoclave (Microclave reactor from Autoclave Engineers) was charged with 250 mg glucose, 150 mg of one of the catalysts: HY 2.6, HY 6, HY 30, Hbeta 12.5, Hbeta 19, Hbeta 150, and HZSM-5 (purchased from Zeolyst International, USA) and 10 mL solvent (methanol, ethanol, propanol or butanol) and then pressurized with argon (20 bar). The autoclave was heated to 160° C. and the stirring was started at 300 rpm once the temperature reached 150° C. After 20 hours of stirring, the autoclave was quenched with cold water and 50 mg naphthalene (internal standard) added to the reaction mixture and the content thereafter analyzed. Aliquots of the reaction mixtures were subjected to GC-FID analysis (Agilent 6890N instrument, HP-5 capillary column 30.0 m×320 μm×0.25 μm). The reaction mixtures were also analyzed by HPLC with RI detection (Agilent 1200 series, 30 cm Aminex© HPX-87H column, 0.005 M aqueous sulfuric acid solution as eluent at a flow rate of 0.6 ml/min). An Agilent 6850 GC system coupled with an Agilent 5975C mass detector was used for qualitative analysis. Sugar conversions to levulinic acid esters were determined by HPLC. The amounts of unreacted monosaccharides were calculated from their individual HPLC standards. Sucrose inverts to fructose and glucose on the acidic HPLC-column used, and the conversions were calculated from the monosaccharides fructose, glucose and mannose on a carbon-basis. The yield of levulinate esters were calculated from GC results on series of individual levulinate ester standards with naphthalene as internal standard. The results are shown in Tables 3 and 7.

Example 2a-d

A 50 ml autoclave (Microclave reactor from Autoclave Engineers) was charged with 250 mg of fructose, 150 mg of a catalyst (HY 6, Hbeta 19), and 10 ml solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) added and the reaction mixture analyzed as described in examples 1. The results are shown in Tables 4, 5 and 6.

Example 3a-d

A 50 ml autoclave (Microclave reactor from Autoclave Engineers) was charged with 250 mg of mannose, 150 mg of a catalyst (HY 6, Hbeta 19), and 10 ml solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) added and the reaction mixture analyzed as described in examples 1. The results are shown in the Tables 5 and 6.

Example 4a-d

A 50 ml autoclave (Microclave reactor from Autoclave Engineers) was charged with 237.5 mg of sucrose, 150 mg of a catalyst (HY 6, Hbeta 19), and 10 ml solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) added and the reaction mixture analyzed as described in examples 1. The results are shown in Tables 5 and 6.

Example 5a-d

A 50 ml autoclave (Microclave reactor from Autoclave Engineers) was charged with 237.5 mg of cellobiose, 150 mg of a catalyst (HY 6, Hbeta 19), and 10 ml solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) added and the reaction mixture analyzed as described in examples 1. The results are shown in Tables 5 and 6.

Example 6a-d

A 50 ml autoclave (Microclave reactor from Autoclave Engineers) was charged with 225 mg inulin, 150 mg of a catalyst (HY 6, Hbeta 19), and 10 ml solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) added and the reaction mixture analyzed as described in examples 1. The results are shown in Table 5 and 6.

Example 7a-c

A 50 ml autoclave (Microclave reactor from Autoclave Engineers) was charged with 225 mg cellulose, 150 mg of the catalyst HY 6, and 10 ml methanol and then pressurized with argon (20 bar). The autoclave was heated to 160, 180 and 200° C. respectively and the stirring was started once the temperature reached 10 to 20° C. below the set temperature (300 rpm). After 20 hours of stirring, the autoclave was quenched with cold water, 50 mg naphthalene (internal standard) added and the reaction mixture analyzed as described in examples 1. The results are shown in Table 5.

Example 8a-e

A 50 ml autoclave (Microclave reactor from Autoclave Engineers) was charged with 250 mg glucose, 150 mg of the catalyst HY 6, and 10 mL methanol and then pressurized with argon (20 bar). The autoclave was heated to 160° C. and the stirring was started once the temperature reached 150° C. (300 rpm). After 10 minutes, 30 minutes, 1 hour, 3 hours and 20 hours of stirring, the autoclave was quenched with cold water, 50 mg naphthalene (internal standard) added and the reaction mixture analyzed as described in examples 1. The results are shown in Table 9.

Example 9a-e

A 50 ml autoclave (Microclave reactor from Autoclave Engineers) was charged with 250 mg glucose, 150 mg of the catalyst HY 6, and 10 mL methanol and then pressurized with argon (20 bar). The autoclave was heated to 100, 120, 140, 160 and 180° C., respectively and the stirring was started once the temperature reached 10 to 20° C. below the set temperature (300 rpm). After 20 hours of stirring, the autoclave was quenched with cold water, 50 mg naphthalene (internal standard) added and the reaction mixture analyzed as described in examples 1. The results are shown in Table 8.

Example 10a-c

Controls without a Catalyst

A 50 ml autoclave (Microclave reactor from Autoclave Engineers) was charged with 250 mg substrate (glucose, fructose, sucrose), and 10 mL solvent (methanol, ethanol) and then pressurized with argon (20 bar). The autoclave was heated to 160° C. and the stirring was started once the temperature reached 150° C. (300 rpm). After 20 hours of stirring, the autoclave was quenched with cold water, 50 mg naphthalene (internal standard) and the reaction mixture analyzed as described in examples 1. The results are shown in Tables 3 and 4.

Example 11

$NH_3$-TPD Measurement

Figure 3:
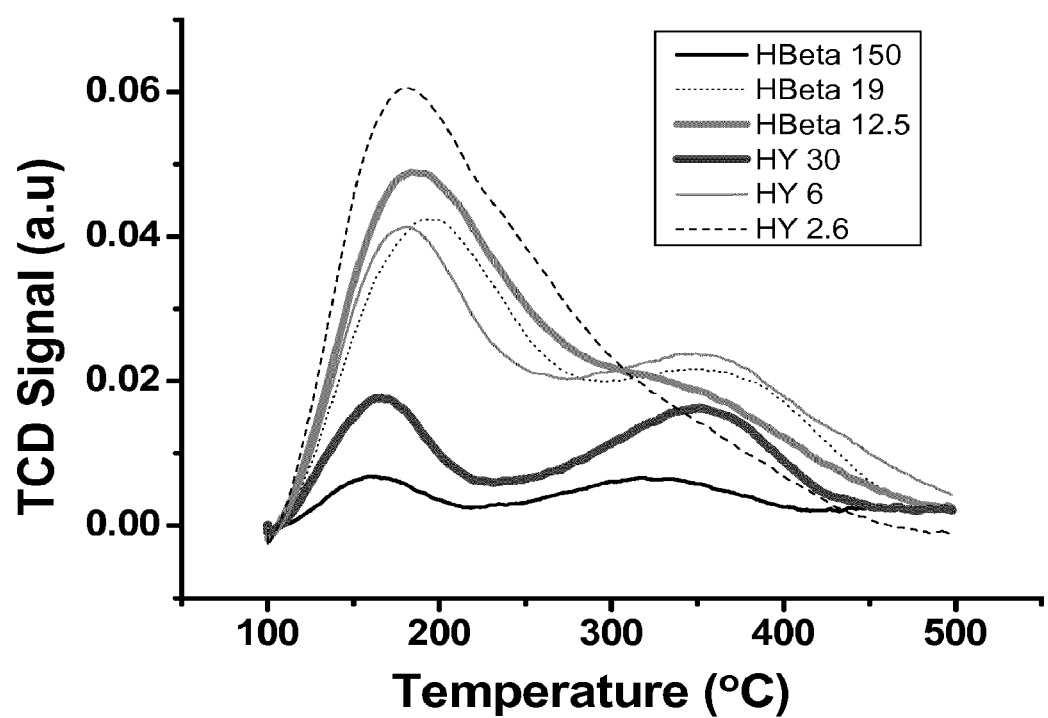
FIG. 3 shows a $NH_3$-TPD profile of Y, Beta and ZSM-5 zeolites.

The number of acid sites present in the zeolites was measured by using a AutoChem II 2920 apparatus from Micromeritics. 100 mg of the sample was placed in a quartz reactor and degassed at 500° C. for 1 hr in a flow of helium at the rate of 50 ml/min. The reactor was then cooled to 100° C. and ammonia (50 ml/min) was allowed to get adsorbed at the same temperature for 2 hr. Before the ammonia desorption measurement, the sample was flushed with helium at the rate of 50 ml/min to remove the physisorbed ammonia. Ammonia desorption was measured every one second from 100 to 500° C. at a ramp of 10° C./min. The number of acid sites is calculated as the area under the curve. The results are shown in Table 2 and in FIG. 3. From the Figure, it can be apparently understood that zeolites contain both medium (approximately between 100 and 270° C.) and strong acid sites (approximately between 270 and 500° C.). The intensity of the peak for HY 2.6 is high at low temperature range (medium acid sites) and low at high temperature range (strong acid sites) compared to HY 6 and Hbeta 19. The yield of methyl levulinate is relatively high for HY6 and Hbeta 19 compared to HY 2.6. The ratio of the number of medium acidic sites (type 1) to strong acidic sites (type 2) can be taken as a measure defining the relative efficiency of the catalysts for the conversion of sugars. A ratio window between 1:03 and 1:1 seem to be a preferred range for the tested catalysts.

The invention claimed is:

1. A method of converting a saccharide into a levulinic acid ester, comprising heating the saccharide to a temperature between 120° C. and 200° C. in the presence of a zeolite or zeotype catalyst with a pore size diameter of at least 6 Å, wherein the effective number of total acid sites (measured by the TPD-NH3 method) in the catalyst is above 250 μmol/g, and the ratio between the number of medium acid sites (type 1) and strong acid sites (type 2) (measured by the TPD-NH3 method) is between 1:0.3 and 1:1; and a $C_1$-$C_4$ alcohol solvent in a pressurized batch reactor;
    wherein the saccharide is selected from the group consisting of fructose, a fructose-containing disaccharide, a fructose-containing oligosaccharide, and a fructose-containing polysaccharide or a mixture thereof; and
    wherein the pressure in the reactor is at least 2 bar.

2. The method according to claim 1, wherein the catalyst has a pore size diameter between 6 and 8 Å.

3. The method according to claim 1, wherein the ratio between the number of medium acid sites (type 1) and strong acid sites (type 2) (measured by the TPD-NH3 method) is between 1:0.3 and 1:0.95.

4. The method according to claim 1, wherein the ratio between the number of medium acid sites (type 1) and strong acid sites (type 2) (measured by the TPD-NH3 method) is between 1:0.5 and 1:0.95.

5. The method according to claim 1, wherein the saccharide is a monosaccharide, a disaccharide, or a polysaccharide, or a combination thereof.

6. The method according claim 1, wherein the catalyst is selected from the group consisting of HY zeolites and Hbeta zeolites.

7. The method according to claim 1, wherein the catalyst is selected from the group consisting of HY 6, HY 30, Hbeta 12.5 and Hbeta 19.

8. The method according to claim 1, wherein the catalyst is selected from the group consisting of HY 6, Hbeta 12.5 and Hbeta 19.

9. The method according to claim 1, wherein the catalyst is a mesozeolite.

10. A method according to claim 1, wherein the $C_1$-$C_4$ alcohol solvent is selected from the group consisting of methanol, ethanol, n-propanol, isopropanol, 1-butanol, 2-butanol and tert-butanol.

11. The method according to claim 1, wherein the saccharide is heated in the solvent in the presence of the catalyst in a pressurized reactor to a suitable temperature at or above 140° C.

12. The method according to claim 11, wherein the saccharide and solvent is heated in the pressurized reactor to or above 160° C.

13. The method according to claim 1, wherein the pressure in the reactor is about 20 bar.

14. The method according to claim 1, wherein the levulinic acid ester is methyl levulinate (MLevu) or ethyl levulinate (ELevu).

15. The method according to claim 1, wherein the levulinic acid ester is methyl levulinate (MLevu).

16. The method according to claim 15, wherein the yield of methyl levulinate (MLevu) is at least 40%.

17. A method for the manufacture of levulinic acid, wherein the levulinic acid ester obtained according to claim 1 is hydrolyzed to obtain levulinic acid, wherein the hydrolysis is acidic, basic or enzymatic.

18. The method according to claim 1, wherein the saccharide is obtained from a biomass or biowaste.

19. The method according to claim 1, wherein the pressure in the reactor is at least 4 bar.

20. The method according to claim 1, wherein the pressure in the reactor is at least 10 bar.

21. The method according to claim 1, wherein the saccharide is selected from the group consisting of fructose, sucrose and inulin, or a mixture thereof.

* * * * *